United States Patent [19]

Fauran et al.

[11] 4,146,615

[45] Mar. 27, 1979

[54] CHRYSANTHELLUM PLANT EXTRACT

[75] Inventors: Francois Fauran, Castanet Tolosan; Gisele Prat, Talence; Annie Thibault, le Bouscat; Claude Andre-Mouries, Caluire; Henri Combier, Lyon, all of France

[73] Assignee: Laboratoires Sarget, Meriqnac, France

[21] Appl. No.: 870,649

[22] Filed: Jan. 19, 1978

[30] Foreign Application Priority Data

Jan. 20, 1977 [FR] France ................... 77 01488

[51] Int. Cl.$^2$ ............... A61K 35/78; A61K 31/70
[52] U.S. Cl. .............................. 424/195; 424/180

[58] Field of Search ....................... 424/195

Primary Examiner—Donald B. Moyer
Attorney, Agent, or Firm—Oblon, Fisher, Spivak, McClelland & Maier

[57] ABSTRACT

A plant extract rich in triterpenic constituents obtained from chrysanthellum and containing as principle component a triterpenic saponin derivative of echinocystic acid whose glycoside contains rhamnose, glucose and xylose may be prepared by extraction of chrysanthellum plants. The extract has been shown to have pharmacological activity, especially analgesic, anti-inflammatory, capillaroprotective and anti-ulcer activity.

12 Claims, No Drawings

CHRYSANTHELLUM PLANT EXTRACT

BACKGROUND OF THE INVENTION

1. Field of the Invention

This invention concerns a new plant extract rich in triterpenic constituents, a method of obtaining it, and various uses of this extract as a medicament in human and veterinary therapy.

2. Description of the Prior Art

The plants of the genus chrysanthellum (family Compositae) are tropical and equatorial plants of the savannah found in central Africa or South America. French patents Nos. 979M and 70/25,949 describe the aqueous and aqueous-alcoholic extracts, respectively, of chrysanthellum procumbens Rich and chrysanthellum americanum Vatke. French patent No. 74/22,371 describes powdered polyphenolic extracts obtained from plants of the genus chrysanthellum.

Plant extracts have been known to exhibit pharmacological activity depending upon the presence of particular constituents, especially triterpene or steroidal saponins. Thus, it was considered useful to investigate methods of preparing extracts of chrysanthellum and to test these extracts for pharmacological activity.

SUMMARY OF THE INVENTION

Accordingly, one object of the invention is to provide a method for preparing extracts of chrysanthellum.

Another object of the invention is to provide medicaments for human and veterinary therapy comprising extracts of chrysanthellum.

Briefly, these objects and other objects of the invention as hereinafter will become more readily apparent from the following description have been attained by providing a chrysanthellum plant extract which contains as principle component a triterpenic saponin derivative of echinocystic acid, wherein said saponin derivative is characterized by a sugar fraction which comprises rhamnose, glucose and xylose.

DETAILED DESCRIPTION OF THE PREFERRED EMBODIMENTS

According to the present invention, extracts of chrysanthellum are provided which exhibit pharmacological properties, permitting their application in human and veterinary therapy.

The extracts are obtained by a procedure in which the plant material is extracted with a polar organic solvent such as an alcohol, preferably of low molecular weight, a ketone, preferably a dialkyl ketone containing lower alkyl groups, or an aliphatic ester of a low molecular weight acid and alcohol. If the solvent is miscible with water, a solvent-water mixture may be used. Preferably ethyl acetate, acetone, methanol, ethanol or a water-methanol mixture is used. The organic phase is next defatted then concentrated. The triterpenic compounds precipitate out. After filtration, the crude residue is purified by dissolution in a polar organic solvent such as a low molecular weight alcohol and reprecipitation by a less polar organic solvent such as chloroform.

The extract thus obtained contains as a major component, a new saponin, which is a glycoside of echinocystic acid or $\Delta^{12}-\beta$, $16\alpha-$ dihydroxyolean-28-oic acid, containing rhamnose, glucose, and xylose in its glycosidic portion.

Echinocystic acid is a triterpenic sapogenin having the structure:

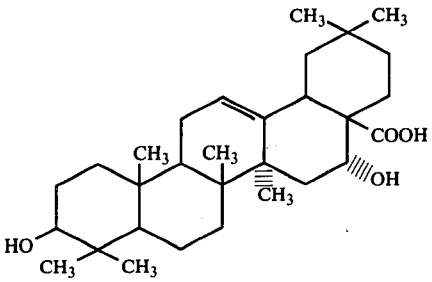

Having generally described this invention, a further understanding can be obtained by reference to certain specific examples which are provided herein for purposes of illustration only and are not intended to be limiting unless otherwise specified.

EXAMPLE

Two kg of crushed plant material (flower tops of chrysanthellum procumbene) were extracted with boiling methanol. The resultant liquid extract was evaporated under vacuum at 60° C. down to a volume of 1 liter. Then 1 liter of water and 1 liter of trichloroethylene were added to the concentrated solution. After stirring and decantation, the trichloroethylene was removed. Three more defatting steps were carried out, each using 1 liter of trichloroethylene. The trichloroethylene phase was washed with water. The combined aqueous methanolic phase was concentrated under vacuum at 60° C. to a volume of 0.5 liter, then allowed to sit overnight. The precipitate was filtered out, dissolved in methanol and reprecipitated with chloroform.

The resultant extract was obtained in the form of a light fawn-colored powder which was soluble in water to the extent of 0.2% by weight, and which was highly soluble in alcohols.

Composition of the extract

The extract thus obtained was analyzed by thin layer chromatography on silica with 100:25:10 ethyl acetate:methanol:water as eluting solvent. Development with 40:1:1 acetic acid:p-anisaldehyde:sulfuric acid, followed by activation for 10 minutes at 100° C. showed that a saponin was the major constituent representing 80% of the total extract. The product was revealed as a greenish spot with Rf 0.30–0.35. The composition of the saponin was determined after further purification by silica column chromatography.

The aglycone and the sugar components were obtained by acid hydrolysis with an $H_2SO_4$/dioxane/water mixture for 6 hours. The aqueous phase resulting from the hydrolysis was concentrated and subjected to chromatographic analysis, which established the presence of rhamnose, glucose and xylose. The analytical techniques used may be thin layer chromatography on silica with 100:60:20 n-butanol:isopropanol:water, using Stahl reagent modified for sugars as indicator, paper chromatography in Partridge's solvent (n-butanol:acetic acid:water, 4:1:15) with aniline phthalate development or vapor phase chromatography after silylation.

The precipitate resulting from the hydrolysis contains the aglycone, which has been identified as echinocystic acid by its physicochemical characteristics.

Sapogenin

Mass spectrum

Molecular weight 472 corresponding to the empirical formula $C_{30}H_{48}O_4$.

Principal fragments m/e 264, 246, 231, 219, 207, 189, 201

IR spectrum in KBr:1685–1700 (COOH function), 1390, 1360–1370, 1330–1340, 1310 and 1280–1290 cm$^{-1}$ (characteristic bands of the oleanic series)

M.P. > 300° C.

Sapogenin methylated by diazomethane

IR spectrum 1705–1725 cm$^{-1}$, ester band

Mass spectrum M = 486. Principal fragments m/e 278, 260, 245, 219, 201, 189, 207, 131.

M.P. = 213° C.

$[\alpha]_D = +36°$ (CHCl$_3$)

Acetylated sapogenin

Mass spectrum M = 556, corresponding to the acetylation of 2 hydroxyls

M.P. = 247° C.

$[\alpha]_D = -6°$ (CHCl$_3$)

Silylated sapogenin

Mass spectrum M = 668, corresponding to the silylation of the acid function and two alcohol functions.

These data are consistent with those in the literature concerning echinocystic acid, in particular, Boiteau R., Pasich B., Rastimamangah; *The Triterpenoids in Plant and Animal Physiology* (Gauthier-Villars Press, 1964); Budzikiewicz, Wilson and Djerassi, *Mass Spectrometry in Structural and Stereochemical Problems. XXXII. Pentacyclic Triterpenes*, J. Am. Chem. Soc., 85, 3688-99 (1963).

To illustrate the therapeutic value of the product of the present invention, the pharmacologic results obtained with the extract prepared according to the above Example will be described.

Acute Toxicity

Acute toxicity was determined in the EOPS mouse, the standard Wistar rat and the EOPS Wistar rat for several methods of administration. The products were administered orally in suspension in gum julep, and i.p. and i.v. in a physiological solution neutralized with NaOH.

Table I below shows the maximum tolerated doses (MTD) and the LD 50's determined by the method of Litchfield and Wilcoxon. In all cases the doses are expressed in mg per kg of animal weight.

electrocardiogram were recorded on lead DII. The animals were observed for 120 minutes. The products were administered in solution in physiological serum. The solutions were neutralized with bicarbonate.

For the extract prepared according to the Example, the minimum lethal dose or MLD was between 30 and 75 mg/kg in 30 minutes. Both the arterial pressure and the heart rate decreased at the start of the perfusion with a minimum at 2 minutes. These parameters then increased slightly before decreasing to the point of death by respiratory arrest.

For aescine, the MLD was 30 mg/kg in 30 minutes. Up to 0.1 mg/kg/min, the arterial pressure and the heart and respiratory rates tended to increase. At 1 mg/kg/min a slight hypotension was observed at the beginning of the perfusion; the arterial pressure next increased, then abruptly dropped to end rapidly in death.

Analgesic Activity

Experiments were performed on male mice of the Swiss EOPS strain and two stress-producing stimuli were used: the P.B.Q. test (chemical stimulus) and the hot plate test (thermal stimulus).

P.B.Q. Test

An aqueous alcoholic solution of 0.02% phenyl p-benzoquinone (P.B.Q.) was administered i.p. to the animals; at the end of 5 minutes this induced abdominal contractions and extension of the mice's hind paws.

The test samples were administered i.p. in neutralized physiologic solution 10 minutes before the P.B.Q. The analgesic ED 50 was calculated using regression analysis, expressing the number of contractions as a function of the dose.

Hot Plate Test

This method, a variant of that of Woolfe and McDonald, was used to determine the number of animals which, when placed in a cylinder heated to 56° C., reacted to the thermal stimulus after a time equal to or greater than 150% of the reference time, after i.p. administration of the test sample in neutralized physiologic solution.

Table II shows the ED 50's determined in the P.B.Q. test and the AD 50's determined in the hot plate test. The doses are expressed in mg/kg of animal weight. In the case of the P.B.Q. test, the equations for the regression analysis, as well as the correlation coefficients, are given.

TABLE I

| Product | Mice | | | | | | Standard Wistar Rats | EOPS Wistar Rats | |
|---|---|---|---|---|---|---|---|---|---|
| | Oral | | IP | | IV | | Oral | IP | |
| | MTD | LD 50 | MTD | LD 50 | MTD | LD 50 | MTD | MTD | LD 50 |
| Extract prepared as in the Example | 1600 | >3200 | 15 | 15 – 30 | ≧15 | | ≧1000 | 10 | 13.5 (12.8 – 14.2) |
| β-aescine | | | 2.5 | 3.2 | <1.25 | 2.10 (1.42 – 3.10) | | <6.25 | 11 (7.8 – 15.6) |

Intoxication by Slow IV Perfusion in the Anesthetized Rat

The perfusions were carried out at the rate of 0.375 ml/min for 30 minutes at most on male standard Wistar rats anesthetized with 15% ethyl carbamate. The carotid pressure, the heart rate, the respiration and the

TABLE II

| Product | P.B.Q. Test ED 50 | Hot Plate Test AD 50 |
|---|---|---|
| Extract prepared as in the Example | 2.8 (2.3–3.7) Y = –(4.25 ± 1.04) X + | 5 |

TABLE II-continued

| Product | P.B.Q. Test ED 50 | Hot Plate Test AD 50 |
|---|---|---|
| β-aescine | 24.68<br>R = 0.70<br>2.7 (1.7–7.5)<br>Y = −(4.47 ± 2.8) X +<br>26.97<br>R = 0.50 | 4.5 |
| Phenylbutazone | 14 | 125 |

Anti-Inflammatory Activity

This effect was determined in the edema test with carrageenan in male EOPS Wistar rats. A volume of 0.1 ml of a suspension of 0.5% carrageenan in physiologic serum was injected into the muscle bundle of the metatarsal region of the animal's hind paws. The test sample was administered i.p. in neutralized physiologic solution simultaneously with the carrageenan. The edema was measured by plethysmometry 2, 3 and 6 hours after the administration of carrageenan.

Table III shows the ED 50's expressed in mg/kg of animal weight.

TABLE III

| | Edema from Carrageenan ED 50 | | |
|---|---|---|---|
| Product | 2 Hours | 3 Hours | 6 Hours |
| Extract prepared as in the Example | 3.0 | 3.3 | 4.1 |
| β-aescine | 6.5 | 8.5 | 7.5 |

Effect on the Smooth Muscles

The extract prepared according to the Example showed in vitro a distinct and reproducible contracting effect on rabbit jejunum, guinea pig ileum, and rat ileum at bath concentrations of $5 \times 10^{-5}$ g/ml or above.

Local Anti-Inflammatory Action

This was determined by the technique of edema of the rat ear induced by croton oil according to the method of Le Douarec. The irritant mixture was prepared from two solutions: solution A which contained 10 ml of pyridine, 2.5 ml of water and 12.5 ml of ethyl acetate and in which the test sample was dissolved; solution B, which contained 1 ml of croton oil and 24 ml of ethyl acetate. The two solutions A and B were mixed together before use. Edema was induced by swabbing the ear with a cotton wad moistened with the irritant mixture (about 1 ml of mixture per rat).

Table IV shows the percentage of inhibition of the edema as a function of the concentration of the test sample expressed in mg/ml of mixture.

TABLE IV

| | % of Activity as a Function of Concentration | | | |
|---|---|---|---|---|
| Product | 10 mg/ml | 20 mg/ml | 25 mg/ml | 50 mg/ml |
| Extract prepared as in the Example | 39 | 30 | | |
| Aspirin | | | 27 | 65 |
| β-aescine | 58 | | | |

Capillaroprotector Effects

The capillary resistance was determined by a variant of the method of Charlier R., Hosslet A., and Colot M., Arch. Inter. Physiol. Biochem., 71, 1–45 (1963) in Sprague Dowley EOPS rats. The products were administered i.p.

The capillary permeability was determined by the method of Charlier R., Hosslet A., and Canivet L., Arch. Inter. Physiol. Biochem., 71, 51–63 (1963) in the standard Wistar rat. The products were administered i.p.

Table V shows:
for capillary permeability, the ED 50 as well as the regression analysis equation expressing the effect on the capillary permeability as a function of the dose expressed in mg/kg.
for the capillary resistance, the effect observed in cm Hg/hr units as well as the percentage of animals exhibiting an effect equal to or greater than 25 ucm Hg/hr as a function of the dose administered expressed in mg/kg.

TABLE V

| Product | Capillary Permeability | Capillary Resistance | | |
|---|---|---|---|---|
| | | dose | activity in ucmHg/hour | % of animals with activity ≧25 |
| Extract prepared as in the Example | 12.5 (10–16)<br>Y = (−5.30 ±<br>1.15) X + 132 | 5<br>10 | 36 ± 10<br>56 ± 16 | 90<br>100 |
| Sodium escinate | 12 (10–15)<br>Y = (−6.50 ±<br>1.2) X ± 159 | 5<br>10 | 26 ± 15<br>78 ± 24 | 60<br>100 |
| Control | | | 7 ± 6 | 0 |

Anti-Ulcer Activity

The anti-ulcer activity was determined in female EOPS Wistar rats in the constraint ulcer test by the technique of Bonfils.

After 24 hours without food the rats, lightly anesthetized with ether, were immobilized in pliable metal-lattice corselets. The paws were tied together in pairs. The rats were suspended in their cages so that they could not touch any point of support. Just before anesthesia the test samples were administered PO in suspension in gum julep in a volume of 0.5 cc/100g. The animals were left constrained for 24 hours and then killed with ether. The stomachs were removed and cut along the greatest curvature. They were stretched out on cork slabs covered with glazed paper to facilitate examination and photographing. A scale of 0 to 4 was used for the number and dimension of ulcerations (0 for no ulceration, 4 for more than 4 ulcers or a perforation).

Table VI shows the percentage of inhibitive activity as a function of the dose administered, expressed in mg/kg.

TABLE VI

| Product | Dose Administered | % of Mortality in the Course of Experiment | % of Anti-Ulcer Activity |
|---|---|---|---|
| Extract prepared as in the Example | 250<br>500 | 0<br>8.3 | 26<br>54 |
| β-aescine | 50<br>125 | 0<br>80 | 13 |

In view of its harmacologic properties, such as analgesic activity, anti-inflammatory activity manifested both generally and locally, capillaroprotective effect, and anti-ulcer activity, the extract prepared according to the present invention could be used as a curative or preventive in phlebology, rheumatology, traumatology, or, for example, in the course of treatment of varicose veins, hemorrhoids, edemas, periphlebitis, purpuras, arterial hypertension, hemorrhegic syndromes, maladies of the connective tissues and ulcers.

This extract, in pharmacologically acceptable vehicles, may be administered orally, for example, in the form of tablets, capsules, coated pills, drops, syrups, ampules of 10 to 200 mg doses per day to be taken two or three times daily or locally in the form of ointments, gels, creams and powders.

This extract may be used in combination with other substances such as vasodilators, steroidal or non-steroidal anti-inflammatories, antibodies and vitamins.

Two examples are given below, by way of non-restrictive examples.

| Tablets: | |
| --- | --- |
| Extract prepared as in the Example | 20 mg |
| Inert material qsp | 1 tablet |
| Ointment: | |
| Extract prepared as in the Example | 3 g |
| Inert material with a base of polyethylene glycol 400 and 4000 and of distilled water qsp | 100 g |

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A method for obtaining an extract having pharmaceutical properties which comprises treating plants of the genus chrysanthellum with a polar organic solvent to obtain an extract, treating the dissolved organic phase to defat and concentrate the pharmaceutical values as a crude precipitate, filtering the crude precipitate, dissolving the precipitate in a low molecular weight organic solvent and reprecipitating the pharmaceutical values with a less polar organic solvent.

2. The method of claim 1, wherein said polar organic solvent is selected from the group consisting of lower alcohols, lower dialkyl ketones, esters of lower alkyl acids and alcohols, and aqueous mixtures thereof.

3. The method of claim 1, wherein said polar organic solvent is selected from the group consisting of ethyl acetate, acetone, methanol, ethanol, aqueous methanol, and aqueous ethanol.

4. The method of claim 3, wherein said defatting comprises concentrating said extract, adding water, and washing with trichloroethylene.

5. The method of claim 3, wherein the less polar organic solvent is chloroform.

6. An extract of chrysanthellum plant prepared by the method of claim 5.

7. An extract of chrysanthellum plant prepared by the method of claim 3.

8. The method of claim 1, wherein the extract contains as a principal component, a triterpenic saponin derivative of echinocystic acid.

9. An extract of chrysanthellum plant prepared by the method of claim 8.

10. An extract of chrysanthellum plant prepared by the method of claim 1.

11. A method for obtaining an extract having pharmaceutical properties from a plant of the genus chrysanthellum which comprises crushing the flower tops of chrysanthellum procumbens, treating the crushed plant with boiling methanol, concentrating the organic extract under vacuum at 60° C., defatting the concentrate with water and trichloroethylene, filtering the precipitate obtained, dissolving the precipitate with methanol and then reprecipitating the pharmaceutical values with chloroform.

12. An extract of chrysanthellum procumbens prepared by the method of claim 11.

* * * * *